United States Patent [19]

Loeb

[11] 4,378,016

[45] Mar. 29, 1983

[54] ARTIFICIAL ENDOCRINE GLAND CONTAINING HORMONE-PRODUCING CELLS

[75] Inventor: Marvin P. Loeb, Chicago, Ill.

[73] Assignee: Biotek, Inc., Arlington Heights, Ill.

[21] Appl. No.: 283,610

[22] Filed: Jul. 15, 1981

[51] Int. Cl.³ .............................................. A61M 7/00
[52] U.S. Cl. ...................................... 128/260; 424/19
[58] Field of Search ............... 128/130, 260, 261, 268; 424/14–22, 81; 3/1

[56] References Cited

U.S. PATENT DOCUMENTS 3,093,831  6/1963  Jordan .................................. 128/260
4,298,002  11/1981  Ronel et al. .......................... 128/260

OTHER PUBLICATIONS

"An Artificial Endocrine Pancreas Containing Cultured Islets of Langerhans", *Artificial Organs*, vol. 4, No. 4, 11–1980, Sun et al., pp. 275–278.

*Primary Examiner*—Richard J. Apley
*Assistant Examiner*—T. J. Wallen

[57] ABSTRACT

An artifical endocrine gland for supplying a hormone to a patient including an implantable housing placed in the body and having an impermeable extracorpeal segment and a semipermeable subcutaneous segment. A replaceable envelope containing live hormone-producing cells such as pancreatic islet cells is then removably positioned in the housing to provide hormones to the patient.

35 Claims, 9 Drawing Figures

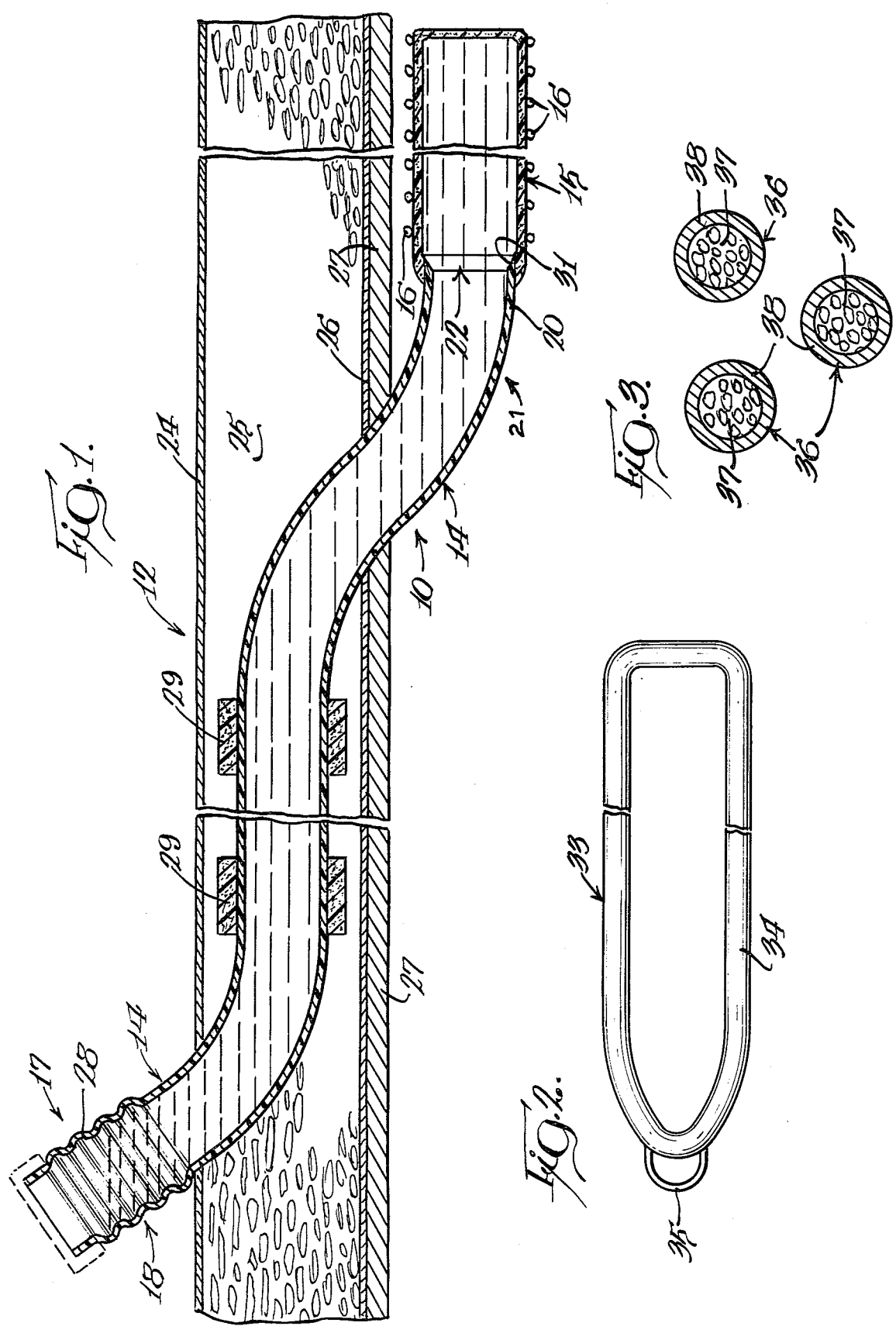

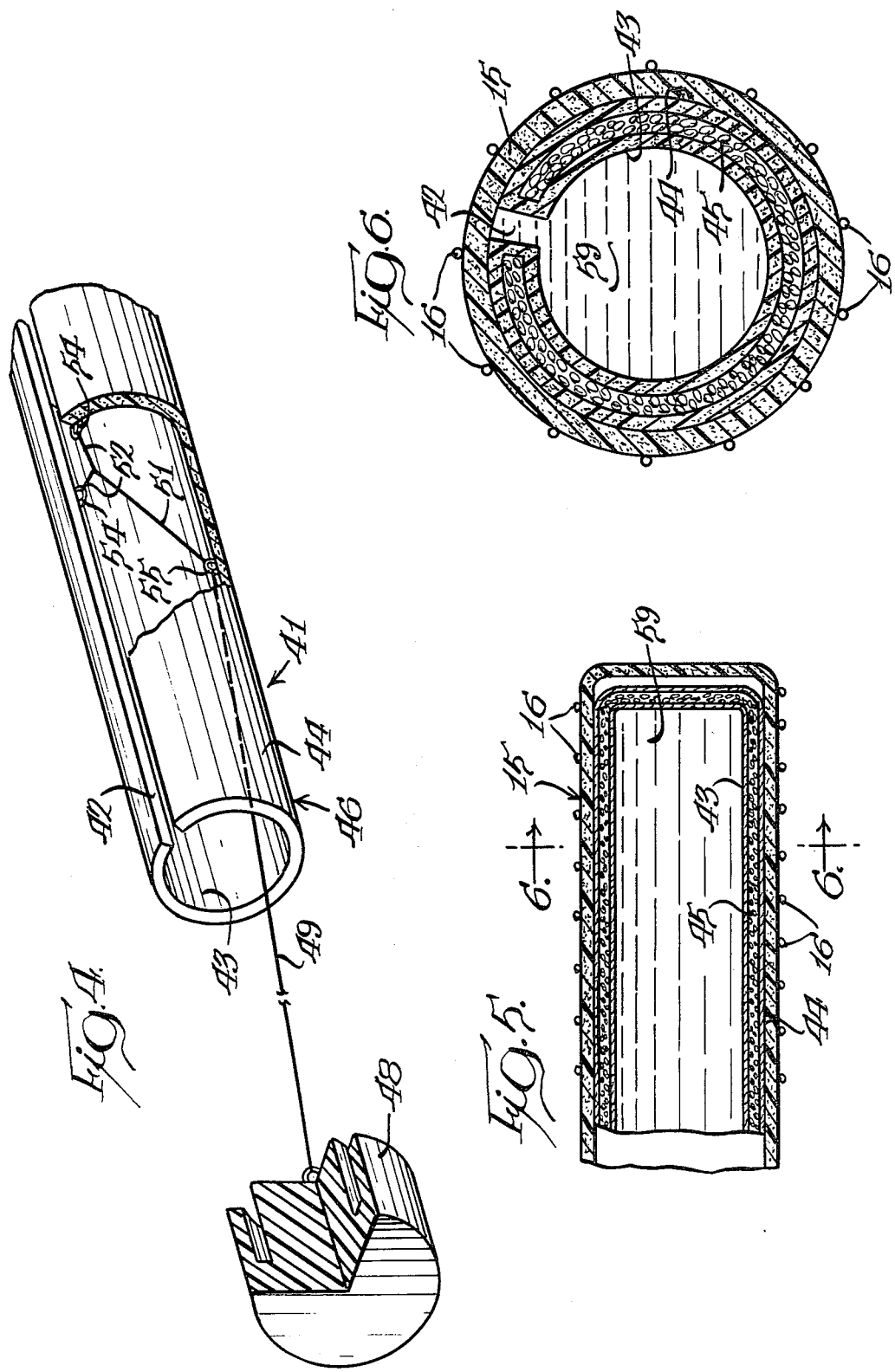

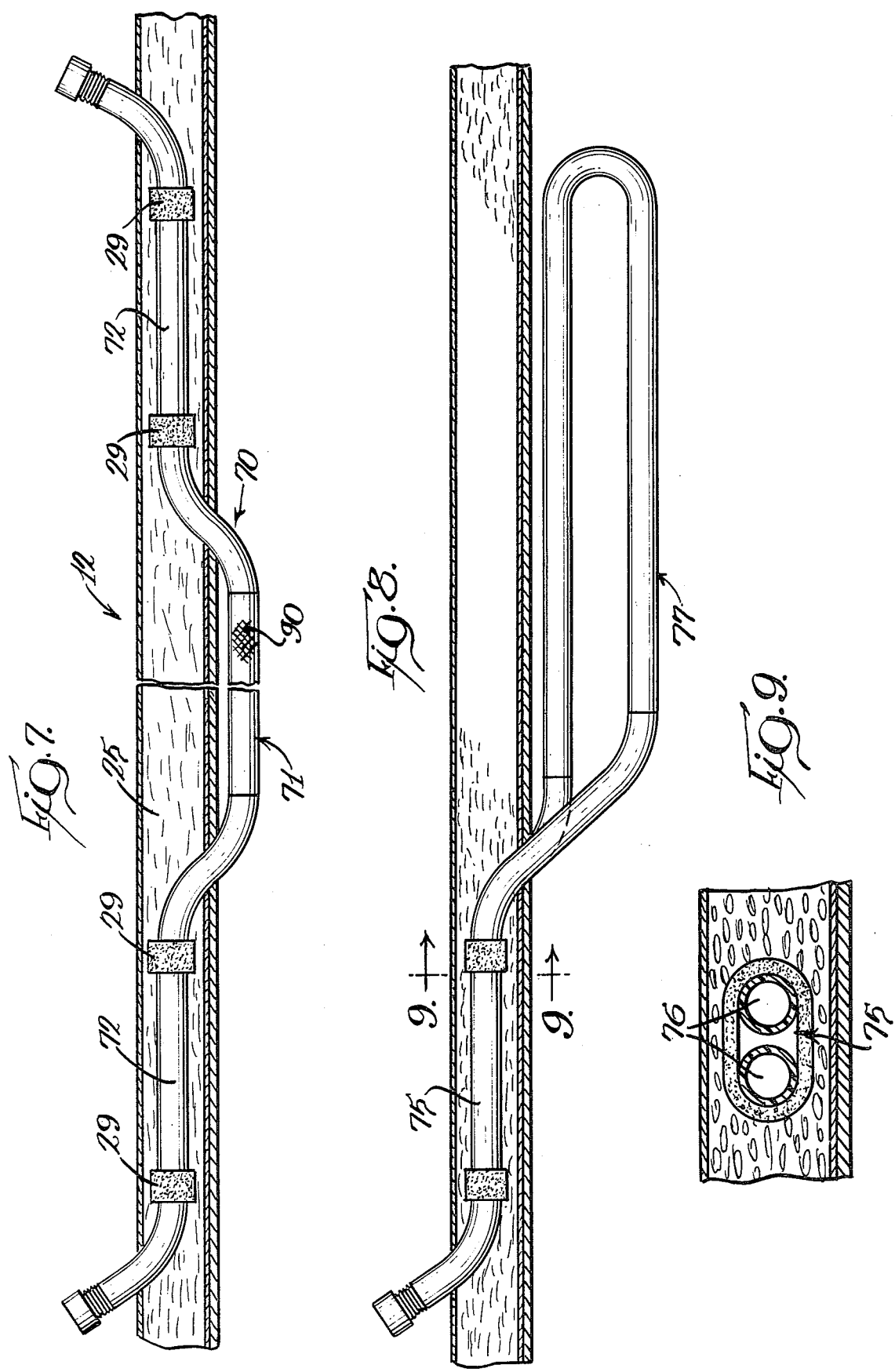

4,378,016

ARTIFICIAL ENDOCRINE GLAND CONTAINING HORMONE-PRODUCING CELLS

TECHNICAL FIELD

This invention relates to artificial hormone-producing glands and more particularly to a structure and method for replaceably implanting live hormone-producing cells within a patient.

BACKGROUND OF THE INVENTION

Many diseases of the body are caused by a deficiency of certain endocrine gland hormones. These diseases include myxedema and diabetes mellitus. The endocrine glands are usually considered to include the thyroid, parathyroid, thymus, pituitary, pineal, adrenal, pancreas and the gonads. While a few hormones, e.g. thyroid hormone, may be taken orally, most hormones are digestable and must be injected.

There are several disadvantages with periodic injection of hormones. Since injections are painful and troublesome, and each injection represents a possibility for infection, injections are spaced at intervals as far apart as possible, resulting in peak and valley hormone concentrations. It has been found that more effective treatment results from a constant supply of hormones in accordance with the body's need. Constant control of the hormone level avoids the problems of peaks and valleys in medication.

To date, the best known detector to measure the body's demand for a particular hormone is the cell of the gland which produces that hormone. Such a cell not only measures the body's need, but also produces the necessary dosage of that hormone. The advantages of such cells are readily apparent in the case of diabetes and insulin demand.

Diabetes mellitus is a disease characterized by hypoglycemia, polyuria, and wasting. It is beneficial to maintain normal blood glucose levels in diabetics at all times, an objective difficult or impossible to achieve using insulin injection and diet. Two solutions have been suggested for achieving more physiologic patterns of insulin replacement. One approach uses a glucose sensor operably associated with an insulin injection system. However an effective glucose sensor has yet to be developed for general use. A second approach implants live insulin producing tissue within the patient.

Transplantation of pancreatic tissue has met with limited success because of immune rejection reactions encountered due to the difficulty in obtaining a perfect tissue match. One solution to this problem is to encapsulate live hormone-producing cells within a membrane capsule. The membrane protects the cells from such reactions but allows the free passage of hormones and nutrients. The encapsulated hormone-producing cells can then either be injected or surgically implanted. For various reasons encapsulated cells once placed in the body only have a limited life span, usually measured in weeks.

Other methods have been to place insulin cells on one side of a membrane while blood flows on the other side of the membrane. However these devices are for extracorporeal use and depend on blood flow access. These devices are not readily adaptable to implantation.

Since no means is presently known to keep implanted pancreatic cells alive and producing insulin at a useful rate indefinitely, periodic replacement is necessary. However, none of the previous implantable devices allow for easy replacement of the cells from outside the body. What is needed is a method and structure for replacing live pancreatic islet cells or other hormone-producing cells from outside the body without having to surgically remove the entire implant.

This invention provides a system and method yielding an artificial endocrine gland with replaceable hormone-producing cells. This invention also provides a system and method yielding an artificial endocrine pancreas which utilizes live pancreatic islet cells as the hormone-producing cells.

SUMMARY OF THE INVENTION

The present invention discloses a method and structure for supplying a patient with hormones in which he may be deficient from implanted hormone producing cells and allowing those cells to be replaced from outside the patient should the need arise.

This is accomplished by implanting in the patient a suitable housing comprising an impermeable hollow stem passing through a body site such as the abdominal wall and a semipermeable membrane sack attached to the stem and positioned inside the patient, e.g., within the peritoneal cavity. The sack allows hormones, nutrients, oxygen and waste products, to flow in and out of the housing while preventing bacteria from entering the patient. The sack may be reinforced by an outer mesh of physiologically compatible material. Live hormone producing cells are contained in a semipermeable membrane envelope positioned within the semipermeable sack. The envelope is permeable to nutrients and hormones, but is impermeable to the hormone-producing cells and immune response bodies.

The implanted cells take over the function of the corresponding natural gland, sense the amount of hormone needed, and produce the correct amount of the desired hormone. The hormone passes through the semipermeable membrane into the patient's body fluids while nutrients, oxygen and in some cases other hormones, pass from the body fluids through the semipermeable membrane to the hormone producing cells. Since an exchange of hormones may take place in both directions through the membrane, the body itself regulates the course of hormone production as with a natural gland.

The present invention is especially useful in the treatment of diabetes where effective control of insulin and glucose levels has proved difficult. Because the semipermeable membrane sack prevents the passage of immune response bodies, it not only allows the use of live cells taken from another human lacking a perfect tissue match, but also the use of live pancreatic cells taken from other animals. A genetically altered organism may also be used for this purpose.

Numerous other features of the present invention will become readily apparent from the following detailed description of the invention and embodiments, from the claims and from the accompanying drawings.

BRIEF DESCRIPTION OF THE DRAWINGS

In the accompanying drawings forming part of the disclosure:

FIG. 1 is a cross-sectional view of a housing shown implanted in a patient;

FIG. 2 is an enlarged plan view of a replaceable envelope having a toroidal configuration;

FIG. 3 is a greatly enlarged cross-sectional view of microencapsulated live hormone-producing cells;

FIG. 4 is a fragmentary cut-away view, partly in section, of a replaceable envelope collar showing a connecting means associated with a plug;

FIG. 5 is a fragmentary cross-sectional view, including an enlarged portion, and showing the replaceable envelope collar as positioned within the housing;

FIG. 6 is a cross-sectional view taken along plane 6—6 of FIG. 5 showing the housing and envelope;

FIG. 7 is a cross-sectional view of another preferred embodiment of the housing having two access ports outside the patient;

FIG. 8 is a cross-sectional view of yet another preferred embodiment similar to FIG. 7 except the two access ports are adjacent; and FIG. 9 is a cross-sectional view taken along plane 9—9 of FIG. 8.

DESCRIPTION OF THE PREFERRED EMBODIMENTS

While this invention is susceptible to embodiment of many different forms, there are shown in the drawings and will be described in detail, preferred embodiments of the invention. It should be understood that the present disclosure is to be considered as an exemplification of the principles of the invention and is not intended to limit the invention to the embodiments illustrated.

The precise shapes and sizes of the components described are not essential to the invention unless otherwise indicated. For ease of description, the device of this invention will be described in its normal operating position and such terms as up, down, inside, outside, etc. will be used with reference to this position. The choice of materials is dependent upon the particular application involved and other variables as those skilled in the art will appreciate. The materials have to be physiologically compatible with the patient.

Referring now to the drawings, FIG. 1 shows a housing 10 for placement in the patient. The housing 10 is constituted by an impermeable hollow stem 14 and a semipermeable membrane sack 15. The hollow stem has a distal end 17 defining an extracorporeal segment 18 and a proximal end 20 defining a subcutaneous, e.g., peritoneal, segment 21. The sack 15 is adapted to receive an envelope containing live hormone-producing cells and has an access opening 22 which is coupled to the proximal end 20 of the hollow stem 14. Sack 15 may be reinforced on the outside by a reinforcing means such as mesh 16. The stem 14 defines an access passageway to the sack 15. Although the sack 15 is shown to have a generally tubular shape, it is understood that the sack may have any suitable configuration including a generally flat hollow disk shape.

The housing 10 is surgically implanted in a patient through the abdominal wall. The abdominal wall 12 is shown here to have an epidermis 24, subcutaneous fat 25, fascia 26 and a peritoneal membrane 27. Peritoneal fluid surrounds the sack 15 of the implanted housing 10. The distal end 17 of the hollow stem 14 defines a normally closed access opening and has a flexible zone 28 comprising a plurality of circumferential grooves and extends beyond the body of the patient allowing access to the sack 15 through the hollow stem 14 from outside the body. Preferably, a portion of the subcutaneous segment 21 for placement in the subcutaneous fat 25 is surrounded by one or more porous cuffs 29 which promote ingrowth of tissue to help anchor the stem and help prevent infection. It is more preferred that at least two cuffs be used, and that there be some distance between cuffs to further increase the area for ingrowth of tissue and to decrease the possibility of infection. Implantation of such an access stem is discussed by Tenckhoff et al., "A Bacteriologically Safe Peritoneal Access Device", Trans. Amer. Soc. Artif. Int. Organs 14:181 (1968) which is incorporated by reference to the extent pertinent.

A replaceable envelope containing live hormone-producing cells is received through the hollow stem 14 and into the sack 15. A seal means is then placed over the distal end 17 of the hollow stem to seal the housing. The replaceable envelope can be removed by a similar process. As it is removed, the envelope contacts the camming surfaces 31 of the hollow stem 14 which help collapse the replaceable envelope to facilitate its removal.

One preferred configuration for the replaceable envelope is toroidal envelope 33 as shown in FIG. 2. The toroidal envelope 33 comprises a semipermeable membrane tube 34 retaining live hormone producing cells within the tube. A withdrawal tab 35 connected to the envelope 33 allows the use of forceps (not shown) or a like implement to insert and remove the envelope from outside the body. A length of monofilament line may also be attached to the withdrawal tab 35. The structure and composition of the membrane will be discussed in greater detail below.

Another preferred configuration for the envelope is shown in FIG. 3. Here the membrane envelope comprises microencapsulated live hormone-producing cells 37 surrounded by a semipermeable membrane 38. Each microcapsule 36 has a diameter of approximately 100–300 microns, allowing a plurality of such microcapsules to be placed in the sack 15. Because of their small size, the microcapsules 36 have a high surface area to volume ratio allowing ready access of nutrients and oxygen to the cells 37 and dispersal of the hormone produced and waste products from the cells. A method of producing such microencapsulated cells is disclosed by Lim et al., "Microencapsulated Islets As Bio-Artificial Endocrine Pancreas", Science 210:908 (1980) and is incorporated by reference to the extent pertinent.

A further preferred envelope configuration is set forth in FIGS. 4–6 and includes a flexible envelope collar 41 defining an open slot 42. The collar 41 has a first end 46 and is comprised of an inner membrane 43 and an outer membrane 44 which encase a substantially unicellular layer of live hormone-producing cells 45. A substantially unicellular layer i.e., a monolayer of live cells completely covering the membrane to a depth of one cell, is employed for two reasons: first to provide maximum surface area to volume ratio and second to discourage de-differentiation of the cells. Effective preparation of a insulin-producing monolayer comprising mostly Beta cells is disclosed by Chick et al., "Pancreatic Beta Cell Culture: Preparation of Purified Monolayers", Endo 96:637 (1975). Using techniques well known to those in the art, either the inner or outer membrane or both, are treated or placed in contact with the live cells until cell attachment forms a substantially unicellular layer on that surface. However, it is not essential that the cells be in a unicellular or monocellular layer as long as diffusion of nutrients and hormones is possible to and from the cells.

The seal means, a plug 48, is used to seal the distal end 17 of the hollow stem 14. The plug 48 is multifaceted to inhibit bacteria from entering the housing 10. The plug 48 may be linked to any one of the replaceable envelopes by a connecting means such as a monofilament line 49 to aid in the removal of an envelope from the housing 10. In use with the envelope collar 41, the connecting means can also include a collar collapsing means 51 which comprises segments of monofilament lines 52 or the like attached to the envelope collar 41 at attachment points 54 near the open slot 42 in the collar 41. The line segments 52 are then attached to the monofilament line 49 which in turn passes through a ring or tube segment 55 attached to the inner membrane 43 of the envelope collar 41 approximately opposite the slot 42.

As tension is placed upon the monofilament line 49, the slot 42 is closed and the collar 41 is partially collapsed, its diameter reduced, to facilitate easy removal from the sack 15. It is advantageous that the attachment points 54 be placed approximately mid-length along the envelope 41 or slightly toward the first end 46 from mid-length. This allows the collar 41 to become tapered when collapsed, the first end 46 becoming the smallest, to aid in removing the collar from the housing 10. In the event envelope 41 binds against the hollow stem during removal, additional tension on lines 49, 51 and 52 will collapse envelope 41 further.

As can be seen in FIGS. 5 and 6, the flexible envelope collar fits snugly within the sack 15 to minimize the distance nutrients and hormones would have to pass to and from the peritoneal fluid. This snug fit is maintained by the natural resiliency of the collar 41 as it expands against the sack 15. Minimizing the distance nutrients and hormones have to pass helps maintain the cells in a viable condition and allows for a faster response time, i.e. it takes less time for the patient's hormone need to be communicated to the cells and for the hormone produced to be released in the body. The membrane sack 15 may also be filled with a nutrient fluid 59 to help keep the hormone-producing cells alive.

Instead of a housing it is also possible to use a loop or hose as shown in FIG. 7. The hose 70 comprises a tube 71 and two, impermeable membrane hollow stems 72, each being like the stem 14 shown in FIG. 1. The membrane envelope may be inserted or removed through either stem. This simplifies placement and removal of the envelope and allows easier maintenance of the inside of the implant. The inside of the hose 70 may be swabbed with an antiseptic during replacement of the envelope.

The access stems of FIG. 7 can be fused into one common region as shown in FIGS. 8 and 9. Such a combination stem 75 having two passageways 76 enters the body at one site only. Each passageway is connected to each end of the tube 77 in a manner similar to that shown in FIG. 7 providing a loop that allows placement or removal of the envelope through either end. By having both passageways pass through the same site, the possibility of infection is further reduced.

Many materials can be used to form the membrane sack 15, the envelopes, and the tubes. Examples of suitable materials are cellulose, cellulose hydrate, cellulose acetate, various cellulose esters, polycarbonate membranes of the type disclosed in U.S. Pat. Nos. 4,075,108 and 4,160,791 to Higley et al., poly(vinyl alcohol) membranes of the type described in U.S. Pat. No. 4,073,733 to Yamauchi et al., microporous poly(ethylene) and poly(propylene) films, cross linked alginate (a non-toxic polysaccharide), poly(2-hydroxyethylmethacrylate) and poly(2,3-dihydroxypropylmethacrylate) films, and the like. The preparation of such membranes is disclosed in U.S. Pat. No. 4,075,092 to White et al., Klomp et al., "Hydrogels for Encapsulation of Pancreatic Islet Cells", Trans. Amer. Soc. Artif. Int. Organs 25:74 (1979), Lim et al. "Microencapsulated Islets as Bioartificial Endrocine Pancreas", Science 210:908 (1980), and Lee et al., Handbook of Biomedical Plastics, Pasadena Technology Press, Pasadena, Calif. (1971). All of the foregoing references are incorporated herein by reference to the extent pertinent. PAN (a polyacrylonitrile membrane available from Rhone-Ponlanc) may also be used. Polycarbonate membranes are particularly advantageous because they are heat sealable and are entirely nonbiodegradable. This allows easy construction and a long life span. One such polycarbonate membrane is BARD PCM available from C. R. Bard, Inc.

A membrane-like filter can be used in place of the membrane. Such a filter, disclosed in U.S. Pat. No. 4,141,838 to Schilling and incorporated herein by reference to the extent pertinent, allows the passage of nutrients, oxygen and hormones and prevents the passage of bacteria and large proteins.

The membrane material chosen may then be treated with heparin to minimize deposits of fibrin in a manner known to those skilled in the art. Illustrative such treatments is the method disclosed in U.S. Pat. No. 3,441,142 to Oja, incorporated herein by reference to the extent pertinent.

The choice of the material for the sack or tube depends on several factors. There should be permeability for desirable molecules such as nutrients, oxygen and hormones, and impermeability to undesirable elements such as bacteria and possibly immune response elements. Generally, pore sizes from about 1.0 to 0.025 microns can be employed, a preferred size being approximately 0.5 microns. This allows the passage of nutrients which generally have molecular weights less than 200, as well as the passage of hormones such as insulin which has a molecular weight of approximately 6400, and prevents the passage of bacteria which may be accidentally introduced within the device. If desired, a membrane size of approximately 0.025 microns can be used to prevent the passage of viruses. In general, it is desirable that the pores be as large as possible, allowing a free flow of nutrients and hormones while still protecting the patient.

To facilitate the transfer of nutrients and hormones, it is desirable that the membrane have a thickness of 200 microns or less. However, membranes of thickness as low as 20 microns can be used as long as they exhibit suitable permeability and adequate strength. The exterior surface of the membrane sack or tube can be reinforced with an open mesh 90 (FIG. 7) made of polyethylene or the like to add resiliency, strength, and resistance to breakage. The sack or tube membrane preferably is treated with heparin to decrease formation of fibrin on the outside surface in contact with the peritoneal fluid.

The envelope membrane is constructed in the same manner as the sack or tube membrane. It is preferred that the envelope membrane be impermeable to such immune response bodies as immunoglobulins which have molecular weights greater than 150,000. Such a membrane would then have a pore size of approximately 50 Angstroms. This is particularly appropriate in view of the fact that some diabetics have antibodies which may react with the islet cells. See, for example, Dobersen et al. "Cytotoxic Autoantibodies to Beta Cells in the Serum of Patients with Insulin Dependent Diabetes Mellitus", N.E. Journ. Med. 303:1493 (1980).

The foregoing specification is intended as illustrative and is not to be taken as limiting. Still other variations within the spirit and scope of this invention are possible and will readily present themselves to those skilled in the art.

What is claimed is:

1. An implantable device for supplying a hormone to a patient comprising:
   (a) a housing constituted by a sack and a hollow stem; the sack having at least one access opening and being constructed of a membrane compatible with body tissue and permeable to body fluid; the hollow stem having a distal end defining an extracorporeal segment and a proximal end defining a subcutaneous segment, the stem being compatible with body tissue and impermeable to body fluids; the sack access opening being sealingly coupled with the proximal end of the stem and together with the stem defining an access passageway to the sack;
   (b) a replaceable envelope containing live hormone-producing cells, the envelope being permeable to nutrients and a hormone; the envelope being removably located within the sack and adapted to pass through the stem; and
   (c) seal means for the access passageway.

2. The implantable device of claim 1 wherein the sack is constructed of material having a pore size small enough to prevent the passage of bacteria.

3. The device of claim 1 wherein the membrane sack is constructed of a membrane-like filter material.

4. The implantable device of claim 1 wherein the replaceable envelope is constructed of membrane-like filter material.

5. The implantable device of claim 1 including at least one porous cuff surrounding a portion of the subcutaneous segment of the hollow stem.

6. The implantable device of claim 1 wherein the replaceable envelope includes a withdrawal tab.

7. The implantable device of claim 1 including a connection means linking the replaceable envelope to the seal means.

8. The implantable device of claim 1 including a nutrient liquid placed within the housing.

9. The implantable device of claim 1 wherein the replaceable envelope has a toroidal configuration.

10. The implantable device of claim 1 wherein the hormone-producing cells are disposed within the replaceable envelope in a substantially unicellular layer.

11. The implantable device of claim 1 wherein the replaceable envelope includes live hormone-producing cells sandwiched between two layers of membrane.

12. The implantable device in accordance with claim 11 wherein the membrane envelope is a flexible collar.

13. The implantable device of claim 1 including an open polyethylene mesh on the exterior surface of the sack to add strength and resistance to breakage.

14. The implantable device of claim 1 including a second stem having a distal end defining an extracorporeal segment and a proximal end defining a subcutaneous segment, the second stem being compatible with body tissue and impermeable to body fluids, and wherein the sack has a tube-like shape having two access openings sealingly coupled with the proximal end of each stem to form a hose with each stem defining an access passageway to the sack.

15. An implantable device for supplying insulin to a patient comprising:
   (a) a housing constituted by a sack and a hollow stem; the sack having at least one access opening and being constructed of a semipermeable membrane compatible with body tissue and permeable to peritoneal fluid but substantially impermeable to bacteria; the hollow stem having a distal end defining an extracorporeal segment and a proximal end defining a subcutaneous segment, the stem being compatible with body tissue and impermeable to body fluids; the sack access opening being sealingly coupled with the proximal end of the stem and together with the stem defining an access passageway to the sack, the housing being adapted to be implanted in the patient with the extracorporeal segment extending outside the body of the patient;
   (b) a replaceable semipermeable membrane envelope containing live pancreatic islet cells, the envelope membrane being permeable to nutrients and insulin but impermeable to the pancreatic cells; the envelope being removeably located within the sack and adapted to pass through the stem; and
   (c) a plug to seal the distal end of the stem.

16. The implantable device of claim 15 including at least one porous cuff surrounding a portion of the subcutaneous segment of the hollow stem.

17. The implantable device of claim 15 wherein the live pancreatic islet cells are disposed in a substantially unicellular layer sandwiched between two layers of membrane to form a flexible collar.

18. The implantable device in accordance with claim 17 including means for collapsing the collar to facilitate removal through the stem.

19. The implantable device of claim 15 wherein the extracorporeal segment includes a flexible zone comprising a plurality of circumferential grooves.

20. The implantable device of claim 15 wherein a plurality of replaceable envelopes are located within the sack.

21. The implantable device of claim 15 wherein the sack has a membrane with an effective pore size of about 0.025 to about 0.5 microns.

22. The implantable device of claim 15 wherein the replaceable envelope has a membrane with an effective pore size of no more than about 50 angstroms.

23. The implantable device of claim 15 including an open polyethylene mesh on the exterior surface of the sack to add strength and resistance to breakage.

24. An implantable device for supplying hormones to a patient comprising:
   (a) a hose constituted by a tube and two hollow stems; the tube having two open ends and being constructed of a membrane compatible with body tissue and permeable to body fluids; each stem having a distal end defining an extracorporeal segment and a proximal end defining a subcutaneous segment, each stem being compatible with body tissue and impermeable to body fluids; each end of the tube sealingly coupled with the proximal end of each stem such that each stem defines an access passageway to the tube;
   (b) a replaceable envelope containing live hormone-producing cells, the envelope being permeable to nutrients and a hormone; the envelope being removeably located within the sack and adapted to pass through either stem; and
   (c) seal means for each access passageway.

25. The implantable device of claim 24 wherein the tube is constructed of a semipermeable membrane impermeable to bacteria.

26. The implantable device of claim 24 including at least one porous cuff surrounding a portion of the subcutaneous segment of each hollow stem.

27. The implantable device of claim 24 wherein the hormone-producing cells are disposed in a substantially unicellular layer sandwiched between two layers of membrane to form an expandable collar.

28. The device of claim 24 wherein the hormone-producing cells comprise pancreatic islet cells.

29. The implantable device of claim 24 wherein the tube has a membrane with an effective pore size of about 0.025 to about 0.5 microns.

30. The implantable device of claim 24 wherein the replaceable envelope has a membrane with an effective pore size of no more than about 50 angstroms.

31. The implantable device of claim 24 including an open polyethylene mesh on the exterior surface of the sack to add strength and resistance to breakage.

32. A method for supplying hormones to a patient comprising:
(a) positioning an elongated housing having one open end in the patient, one end of the housing within the patient and having a semipermeable membrane wall and the other, open end of the housing extending outside the body;
(b) removably placing into the housing a semipermeable membrane envelope containing live hormone-producing cells; and
(c) sealing the open end of the housing with a plug.

33. The method of claim 32, wherein the membrane wall placed in the patient is of material having a pore size sufficient to prevent the passage of bacteria.

34. The method of claim 32 including placing a nutrient liquid in the housing.

35. The method of claim 32 wherein the envelope of hormone-producing cells placed into the housing contains live pancreatic islet cells.

* * * * *